United States Patent [19]

Tice et al.

[11] Patent Number: 4,798,786
[45] Date of Patent: Jan. 17, 1989

[54] LIVING CELLS ENCAPSULATED IN CROSSLINKED PROTEIN

[75] Inventors: Thomas R. Tice, Birmingham; William E. Meyers, Helena, both of Ala.

[73] Assignee: Stolle Research and Development Corporation, Cincinnati, Ohio

[21] Appl. No.: 375,710

[22] Filed: May 6, 1982

[51] Int. Cl.$^4$ .................... C12N 11/02; C12N 11/10; C12N 11/04; C12N 5/02
[52] U.S. Cl. .................... 435/177; 424/93; 435/178; 435/182; 435/240.22; 435/240.25; 435/252.1
[58] Field of Search ............... 435/174, 177, 178, 182, 435/240, 241; 424/36, 94, 93; 252/316

[56] References Cited

U.S. PATENT DOCUMENTS

| | | | |
|---|---|---|---|
| 2,889,252 | 6/1959 | Valentine | 424/36 X |
| 3,137,631 | 6/1964 | Soloway | 424/36 X |
| 3,516,942 | 6/1970 | Scarpelli | 252/316 |
| 3,642,978 | 2/1972 | Ogawa | 424/37 |
| 3,664,963 | 5/1972 | Pasin | 252/316 |
| 3,691,090 | 9/1972 | Kitajima et al. | 252/316 |
| 3,714,065 | 1/1973 | Kitajima et al. | 252/316 |
| 3,780,195 | 12/1973 | Balassa | 426/350 |
| 3,838,007 | 9/1974 | Van Velzen | 435/177 X |
| 3,937,668 | 2/1976 | Zolle | 252/316 |
| 4,024,233 | 5/1977 | Winchell | 424/1 |
| 4,094,965 | 6/1978 | Layne et al. | 252/316 X |
| 4,107,288 | 8/1978 | Oppenheim et al. | 424/22 |
| 4,147,767 | 4/1979 | Yapel, Jr. | 424/36 X |
| 4,187,285 | 2/1980 | Meeks et al. | 424/1 |
| 4,251,387 | 2/1981 | Lim et al. | 424/94 X |
| 4,255,411 | 3/1981 | Lim et al. | 424/1 |
| 4,257,884 | 3/1981 | Lim | 435/182 X |
| 4,324,683 | 4/1982 | Lim et al. | 424/94 X |
| 4,352,883 | 10/1982 | Lim | 435/182 X |
| 4,353,888 | 10/1982 | Sefton | 435/240 X |

OTHER PUBLICATIONS

Chang, T. M. S., Encapsulation of Enzymes, Cell Contents, Cells, Vaccines, Antigens, Antiserum, Cofactors, Hormones and Proteins, Biomedical Applications of Immobilized Enzymes and Proteins, vol. 1, Plenum Press, 1977 (pp. 69, 83-88 & 151-153).
Chang, T. M. S., Semipermeable Microcapsules, Science, vol. 246, 1964 (pp. 524-525).
Business Week: Jan. 11, 1982, pp. 122-123.
*Genetic Engineering News*, "At Damon, Microencapsulated Monoclonal Antibodies", Mar./Apr. 1982 (pp. 24-25).

*Primary Examiner*—David M. Naff
*Attorney, Agent, or Firm*—Oblon, Fisher, Spivak, McClelland & Maier

[57] ABSTRACT

Living cells are encapsulated by: (a) dispersing living cells in an aqueous solution of a capsule wall-forming protein; (b) forming aqueous droplets of the cell containing dispersion in an aqueous-immiscible, cell compatible continuous processing medium; and (c) crosslinking the protein with a crosslinking agent which is soluble in the continuous processing medium but substantially insoluble in the aqueous droplets. The resultant capsules containing living cells may be treated with a capsule wall degrading enzyme to enlarge pores of the capsules. The encapsulated cells may be used for administration of cells to an animal for growing the cells in the animal or for delivery to the animal of a substance produced by the cells. By the cells being encapsulated, the cells are not destroyed by the aminal immune system and immune response by the animal may be minimized.

26 Claims, No Drawings

LIVING CELLS ENCAPSULATED IN CROSSLINKED PROTEIN

BACKGROUND OF THE INVENTION

1. Field of the Invention

The present invention relates to encapsulated living cells, their preparation and uses.

2. Brief Description of Prior Art

The use of cells, either of animal or vegetable origin, in vitro, has recently received renewed attention due to a number of important technological developments. For example, in vitro cell cultures of hybridomas are now routinely utilized for the preparation of monoclonal antibodies of great specificity. Cancer cell lines are utilized in vitro for formation of such hybridomas, and also for the screening and testing of potential carcinogenic and anticarcinogenic compounds. Pancreatic cells have been utilized in vitro and in vivo for the production and delivery of insulin. Also, the industrial utilization of isolated immobilized cells has received attention, since these can be used as catalysts for biochemical reactions, and such reactions can be used as important tools in syntheses and analytical determinations (see, for example, *Venkatsubramanian*, "Immobilized Microbial Cells," 106 ACS Symposium Series, (1979)).

In many instances, the direct introduction of a foreign cell into a host can produce severe immune responses in the host. For example, when growing hybridoma cells in the ascites fluid of a host such as a mouse, the mouse has to be pretreated so as to prevent immune response. When injecting whole insulin cells into a human, immune response is also a complicating feature. A need, therefore, exists for improved methods of facilitating the introduction of such cells into a host, as well as generally, for facilitating the manipulation of cells in vitro.

A number of methods has been described in the prior art relating to either the encapsulation or entrapment of biologically active materials, albeit not of living cells.

Lim et al, for example, in U.S. Pat. Nos. 4,251,387, 4,255,411 and 4,257,884, describe techniques for producing semi-permeable microcapsules by interfacial polymerization, and their uses in immunoassays and chromatography. The material to be encapsulated and a hydrophilic monomer are emulsified in a hydrophobic continuous phase. Polymerization is initiated by dissolving a second monomer in the continuous phase, and occurs only at the interface between the hydrophilic droplets and hydrophobic continuous phase, to result in the formation of macroporous, poorly-defined capsule membranes. The affinity of the continuous phase for the hydrophilic monomer is varied by altering the polarity of the continuous phase, and microcapsules having uniform capsule membranes and selected upper limits of permeability can be produced. Balassa, U.S. Pat. No. 3,780,195, describes a process for encapsulating active materials in a shell composition in which the capsule composition is formed by dispersing an active material and a shell composition in a solvent for the shell composition. The capsule composition is formed into particles containing the active material in a dispersed phase, and removing the solvent from the shell composition solution by adding a lower molecular weight polyglycol. Preferably the desolventizing operation can be accelerated by first dispersing the capsule composition in a viscous white mineral oil to form discrete particles, and then admixing the mixture with anhydrous polyglycol. Among the shell materials are included proteins, such as egg and blood albumin. Other patents dealing with the encapsulation of medicaments or (non-living) natural products, are Valentine et al, U.S. Pat. No. 2,889,252, Kitajima et al, U.S. Pat. Nos. 3,691,090 and 3,714,065; Scarpelli, U.S. Pat. No. 3,516,942; Pasin, U.S. Pat. No., 3,664,963; Ogawa, U.S. Pat. No. 3,642,978 and Soloway, U.S. Pat. No. 3,137,631. The Soloway patent discloses encapsulation in natural products such as albumins, followed by treatment with crosslinking agents such as formaldehyde, glyoxal and the like, in order to increase the stability of the capsule walls.

Among patents which describe the formation of soft solid microparticles, not capsules, having homogeneously dispersed therein various medicaments and therapeutic compositions are Meeks et al, U.S. Pat. No. 4,187,285, (technetium-99m dispersed in albumin); Yapel, Jr., U.S. Pat. No. 4,147,767 (drugs dispersed in solid serum albumin); Oppenheim et al, U.S. Pat. No. 4,107,288 (drugs dispersed in particles, including serum albumin particles, which are crosslinked); Zolle, U.S. Pat. No. 3,937,668 (solid albumin particles carrying radioactivity, drugs, insecticides, dyes and the like); Winchell et al, U.S. Pat. No. 4,024,233 (microaggregate human serum albumin having dispersed tin); and Layne et al, U.S. Pat. No. 4,094,965 (tin and a radionuclide dispersed in albumin).

A system for the microencapsulation of a great variety of substances, including antigens of various microorganisms such as bacteria and viruses, is described in copending U.S. application Ser. No. 194,127, filed Oct. 6, 1980, at the U.S. Patent and Trademark Office, for "Microencapsulation Process" by Tice and Lewis, now U.S. Pat. No. 4,389,330. This application is herein incorporated by reference. The microencapsulation process taught in this application comprises dissolving or dispersing an active agent in a solvent, and dissolving wall-forming material in said solvent; dispersing the solvent containing the active agent and wall-forming material in a continuous phase processing medium; evaporating a portion of the solvent from the dispersion step, thereby forming microcapsules containing the active agent in the suspension; and finally extracting the remainder of the solvent from the microcapsules.

The problems confronted by the practitioner in attempting to extend all of these prior art techniques to the encapsulation of living cells, however, are multiple. Many of the techniques described in the prior art operate under conditions which are too drastic for the survival or continuing viability of a living cell. For example, the use of organic solvents, high temperatures, reactive monomers, crosslinking conditions, and the like may hamper the survival of cells intended to be encapsulated. Moreover, it is crucial to prevent dehydration or osmotic rupture of the cell. Another serious problem is the necessity of providing the microcapsule walls with sufficient permeability for nutrients and excretion products Along the same lines, if the cell is used as a source of macromolecules or biological assemblies, such as antibodies or virions, respectively, it is necessary to assure the existence of pores of sufficient size to permit the exit of such macromolecules. If the cells are encapsulated and injected into a host so that they would provide a continuous source of macromolecules or biological assemblies, the pores have to be of the right diameter to allow the transport of the macromolecules or assemblies to the extra capsular medium, yet prevent the entry of molecules or cells of a host which would destroy the encapsulated cells due to the immune system of the host.

A need, therefore, continues to exist for a method to encapsulate living cells under sufficient mild conditions which would allow the living cells to retain viability yet will also allow the formation of a controlled porosity in the capsule walls.

SUMMARY OF THE INVENTION

It is therefore an object of the invention to provide a method for the encapsulation of living cells.

Another object of the invention is to provide encapsulated living cells.

Yet another object of the invention is to provide various uses for the encapsulated living cells.

These and other objects of the invention as will hereinafter become more readily apparent have been attained by providing:

A composition comprising a living cell inside a capsule having a wall comprising a crosslinked protein.

Yet another object has been attained by providing:

A process for the encapsulation of living cells which comprises:

(a) dispersing living cells in an aqueous solution of a capsule wall-forming protein;

(b) forming aqueous droplets of said cell containing dispersion in an aqueous immiscible, cell compatible, continuous processing medium; and (c) crosslinking said protein with a crosslinking agent which is soluble in said continuous processing medium but substantially insoluble in said aqueous droplets.

BRIEF DESCRIPTION OF THE PREFERRED EMBODIMENTS

The present invention provides a mild and efficient method for the preparation of encapsulated living cells. The invention is based on the discovery of conditions which allow the formation of controlled porosity capsule walls, which in turn allow the formation and use of encapsulated cells in such varied areas as hybridoma growth, drug delivery, and the like.

Broadly, the process of the invention comprises three steps:

(a) dispersing living cells in an aqueous solution of a capsule wall-forming protein;

(b) forming aqueous droplets of the cell-containing solution in an aqueous immiscible, cell compatible, continuous processing medium; and (c) crosslinking the protein with a crosslinking agent which is soluble in the continuous processing medium but substantially insoluble in the aqueous droplets.

The first step in the method is the formation of a solution of a protein or proteins which will form the eventual capsule wall. The wall material, therefore, should be soluble in water or in substantially aqueous solutions and should be capable of forming capsules when crosslinked. Suitable water soluble proteins include, for example, casein, collagen, gelatin, soy protein, gluten, albumins, immunoglobulins, and various modifications and derivatives thereof. The wall-forming protein is dissolved in the aqueous solvent, preferably in a minimum practical amount of aqueous solvent. Sufficient aqueous solvent should be used so that the resultant wall-forming composition has a viscosity no higher than practicable to handle with available equipment. Also, the viscosity should be such that a good dispersion of the cells can be obtained therein. For example, a solution containing anywhere between 5 and 95% by weight of protein, preferably 5–25% by weight of protein, can be prepared. At this stage, any antioxidant, preservative, or surfactant may be added if desired.

To the protein-containing wall-forming solution, is added a suspension of the appropriate cells to be encapsulated. The cells, which are described hereinafter, are normally added in an appropriate nutrient-containing medium, such as culture medium containing the necessary salts, reducing agents, antibiotics, serum, buffers, and the like. Culture media for either animal cell lines in vitro or microorganism cells are well-known to those skilled in the art and will not be described any further. The appropriate cells are homogeneously dispersed throughout the wall-forming protein-containing solution, using a mild dispersion method so as to prevent the rupture of the cells. Alternatively, to the wall-forming protein-containing solution is first added the appropriate culture medium, the intermediate solution is sterilized, and to it is then added a pellet or other appropriate form containing the living cells. These cells are then dispersed throughout the suspension. The number of cells to be added to the solution depends on the concentration desired in the microcapsules. Generally, anywhere between $10^3$–$10^{12}$ cells per ml of solution can be used, most preferably $10^4$–$10^8$ cells per ml.

The second step in the process is dispersing the aqueous phase in a continuous processing medium. This processing medium must be immiscible with the aqueous phase. Examples of aqueous immiscible phases include both mineral and non-mineral oils, with the proviso that the continuous medium should be compatible with the living cells, i.e., not harm or interfere with cell metabolism during the time of manufacturing. Appropriate materials may include such oils as silicone oils, peanut oil, cotton seed oil, sesame oil, and the like. A surfactant (emulsifying agent) can be added to the continuous phase processing medium to prevent the microcapsules from agglomerating and to control the size of the aqueous microdroplets in the emulsion. The dispersion can be formed by mechanically agitating the continuous phase processing medium by a device such as a colloid mill, a homogenizer or the like. A simple mechanical stirrer can also be used and is preferred, since it is sufficiently mild to prevent breakdown of the cells. An emulsion can also be formed by adding small drops of the aqueous solution to the continuous phase processing medium. In a preferred embodiment of the dispersion step, the aqueous solution is dispersed in sesame oil.

The temperatures during the formation of the aqueous solution and further dispersion of the solution in the processing medium are not especially critical, but can influence the size and quality of the microcapsules. Moreover, depending on the continuous phase processing medium employed, the temperature must not be too low or the aqueous solvent and processing medium will solidify, or the processing medium will become too viscous for practical purposes. Alternatively, the temperature should not be so high that the processing medium will evaporate, or the cells will lose their viability. Accordingly, the dispersion process can be conducted at any temperature which maintains stable operating conditions. Preferably, the temperatures range from about 0° C. to 40° C., most preferably about 25° C.–37° C.

Any amount of aqueous droplets which will maintain a stable emulsion is appropriate for the second step. The amount of aqueous phase should not be so high that crosslinking between two different droplets will occur, and not be so low that it will be difficult to recover the microcapsules after the process. Ideally, the ratio of aqueous phase to processing medium is anywhere from between 0.1 and 99 parts of aqueous volume to 100 parts of processing medium volume. Most preferably the ratio is between 1 and 50 parts of aqueous phase to 100 parts of processing medium volume.

A crosslinking agent is next added to the stable emulsion of aqueous droplets in the processing medium. The crosslinking agent has a number of functional and structural requirements. First, it should be substantially soluble in the continuous processing medium yet insoluble in the aqueous droplets. This requirement is quite crucial since it is the controlling element in preventing introduction of the crosslinking agent into the aqueous droplets, and therefore possibility of extensive crosslinking of cells either between themselves or with the inside walls of the capsule. Because most cells contain proteins on the surface thereof, and these proteins contain groups which are capable of being crosslinked with the crosslinking reagents, the possibility of substantial aqueous solubility of the crosslinking reagent should be avoided. Since the crosslinking agent is soluble almost exclusively in the nonaqueous continuous phase, the crosslinking reaction occurs mostly at the interface between the aqueous droplets and nonaqueous continuous phase providing an "interfacial-type" crosslinking. A second requirement for the crosslinking agent is that its crosslinking capacity occur at the appropriate manufacturing temperatures. A third requirement for the crosslinking agent is that it be at least bifunctional, so that it can crosslink at least two or more crosslinkable regions on the protein wall material. Fourth, the crosslinking material should contain chemical functions which will readily react under the conditions of the stable emulsion, with naturally occurring functional groups on the protein. Such functional groups include hydroxy groups, amino groups, carboxyl groups, and thiol groups. Most preferably, the amino groups of the protein are utilized, for example the terminal amino groups or the $\epsilon$-groups of lysine. Among the preferred crosslinking agents of the present invention are the oil soluble diacid halides, capable of forming amide bonds with the protein amino groups. For example, such compounds include $XOC-(CH_2)_n-COX$, wherein X is a halide (preferably fluoride, bromide or chloride), and n is usually 4–12. Among the most preferred are adipoyl chloride or sebacoyl chloride. In general, any hydroxy or amine-reacting multifunctional oil soluble crosslinking agent can be used. A fifth requirement is that the crosslinking agent should not react with the continuous phase processing medium.

The concentration of the crosslinking agent in the processing medium can be adjusted quite liberally, and the low limits are those below which it is impossible to form a self supporting capsule wall. The upper limit, on the other hand, is that above which too much crosslinking would occur and the resulting capsule walls become too rigid and impermeable. The upper limit will also depend on the solubility of the crosslinking agent in the continuous phase processing medium. Normally, the concentration can be readily adjusted by one of skill in the art, and can fall between 0.001 to 10 mg/100 ml of processing medium.

The ratio of crosslinking agent to wall-forming protein will depend on the desired "tightness" of the crosslinking, the number of active crosslinkable functional groups present in the particular protein utilized, the size of the droplets, the time of reaction, and the wall thickness. An appropriate ratio would be anywhere between 1 to 1,000 molecules of crosslinking agent per molecule of protein.

After addition of the crosslinking agent, the resulting suspension is continuously stirred to maintain the droplets in emulsion, for a time sufficient to allow the desired amount of crosslinking to occur. The temperature conditions of the crosslinking reaction can be maintained as before, or increased slightly to accelerate crosslinking. Times can range from a few minutes to several hours, preferably 5–10 minutes to 2 hours, most preferably 15 minutes to 1 hour.

In many instances, the resulting suspension of microcapsules in processing medium, can be directly utilized, as for example, in the injection of encapsulated hybridomas into the peritoneal cavity of an animal. This is a preferred method of operation, especially when the processing medium contains little or no crosslinking agent at the end of the reaction and when a bio-compatible processing medium, such as sesame oil, has been utilized in the formation of the capsules. In this mode of operation, the user of the method could simply prepare the microcapsules in situ and inject the resultant dispersion of capsules into the animal.

Optionally, it is of course possible to add a number of other steps, such as separation of the capsules from the processing medium, and washing thereof with aqueous and/or nonaqueous washing solutions. The separation can be appropriately carried out by interrupting the stirring, followed by decantation or centrifugation. It is also possible to simply layer the processing medium on an aqueous phase, and centrifuge the bilayered arrangement, so as to directly force the microparticles from the processing medium into the aqueous phase. Preferably, the aqueous phase would be an appropriate culture medium for further growth of the encapsulted cells.

In a preferred embodiment of the invention, the starting protein solution contains a water soluble poragenic (i.e., pore forming or generating) compound, such as poly(vinyl alcohol), carboxymethyl cellulose, poly(vinyl pyrrolidone), starch or a glycol, most preferably glycol, such as a polyhydric glycol. The presence of this compound protects the cells during encapsulation, and assists in the formation of pores in the capsule walls. It is speculated that the poragenic compound may become entrapped between protein molecules during the crosslinking operation, and is removed during the subsequent contact of the formed capsules with aqueous solution, leaving pores in the walls of the capsules. The amount of poragenic compound used can be varied over a relatively wide range, and depends on the number of cells, the amount of porosity desired, the solubility of the poragen and the volume of the capsule compositions. The concentration in the aqueous solution can be from 1 mg/ml to 1 g/ml, preferably 200 to 600 mg/ml. Ratios ranging from 1:10 by weight to 10:1 by weight of poragen to protein can be utilized. Polyglycols preferred in the present invention include those having molecular weights in the range from about 100 (e.g., diethylene glycol) to about 10,000. The polyethylene glycols are preferred, especially those having molecular weights from about 4,000 to 6,000, preferably in the upper range.

Another preferred embodiment in the present invention is the adjustment of the pore size of the capsules by contacting the formed capsules with a capsule-wall degradation enzyme. In the case when the capsule wall is exclusively proteinaceous in nature, a proteolytic enzyme such as trypsin or chymotrypsin is added to a buffered aqueous suspension of capsules, and allowed to incubate with the capsules for a time sufficient to enlarge the pores to the desired size. Generally, this time ranges from 1–2 minutes to 1–2 hours, preferably 1–2 minutes to 30 minutes. The enzyme digestion can be stopped, for example, by adding to the capsule dispersion an enzyme inhibitor, such as, for example, a proteolytic inhibitor, e.g., soybean trypsin inhibitor, or by washing away the enzyme from the capsles.

In another preferred embodiment, the cell wall on the capsules is not exclusively composed of a protein material, but contains from 0.1 to 80% by weight of another material that is enzyme degradable, such as, for example, a polysaccharide, keratin, DNA, RNA, collagen or other such materials. After formation of the capsule having a composite wall of protein and other enzyme degradable material, the pore size of the capsule can be enlarged by treating the capsule with an enzyme which degrades the other enzyme degradable material. In case such material is a polysaccharide, a polysaccharide-degrading enzyme could be used. Specifically, a material such as cellulose, collagen, DNA, RNA, starch or keratin can be added, and the pore size expanded with cellulase, collagenase, DNase, RNase, amylase, or keratinase, respectively. The treatment times with the degrading enzyme can be again adjusted as with the proteolytic enzyme, supra.

The capsules of the present invention are particles of a spherical shape, although sometimes the capsules may be irregularly shaped. The capsules can vary in size, ranging from submicron to millimeters in diameter. Preferably, submicron to 250 μm diameters are desirable for formulations allowing administration of the capsules (more specifically "microcapsules") with a standard syringe needle.

The pore sizes are at least those that will allow the entrance and exit of nutrients required to maintain cell growth and viability, and at most those which will prevent the exit of the whole cell. Ideally, the pore sizes are those which will allow the exit of macromolecules having molecular weight ranges from about 10,000 to 500,000, including most known immunoglobulins or virions. Virions normally have diameters of up to about 3,000 Å. Thus pore sizes may range from 5 Angstroms to 15 μm, most preferably 20 Angstroms to 0.3 μm.

The nature and type of cells present in, and capable of being encapsulated in the capsules of the present invention is unlimited. The cells may be of animal origin, vegetable origin, or microbiological origin. The cells may also be of artificial origin such as hybridoma cells. These latter are, in fact, among the preferred types of cells to be encapsulated. Other cells derived from cell lines, such as myeloma cells and the like, can also be encapsulated. Finally, microorganism cells such as bacterial cells can be encapsulated. Among these, the most preferred bacterial cells are those which secrete a pharmacologically useful product, and include novel bacterial strains made by DNA recombination techniques which express materials encoded for by a gene from a foreign, especially mammalian, donor. Bacterial cells expressing foreign genes include those which produce interferon, growth hormones, insulin, (which may be produced by pancreatic cells themselves, of course), other hormone or prohormone-type molecules, and the like.

The number of cells per capsule will depend on the size of the capsule but ranges anywhere from 1 to 1,000, preferably 1–100. During growth and reproduction, the cell density increases inside the capsule, and growth then reaches a saturation level which will vary from cell to cell, and from capsule size to capsule size. A routine amount of experimentation will quickly reveal what the saturation limit is for a particular type of cell/capsule size combination.

The present invention lends itself readily to the preparation of kits, to be utilized by the user for encapsulation of any desired cell. Such a kit can generally comprise a carrier being compartmentalized to carry one or more containers therein such as test tubes, vials, glasses, bulbs, and the like. The container means may include a first means comprising the wall-forming protein with or without other elements of the original solution such as poragen, other enzyme degradable materials, nutrient medium, surfactants, and the like. The wall-forming materials may be present in solution or in freeze-dried form. A second container means may contain an appropriate crosslinking agent. A third container means may contain the water immiscible processing medium. Other container means may contain desired cells, degradation enzymes, other wall-forming materials, and the like. The kit will normally contain instructions in the form of a catalogue, booklet or brochure. In utilizing this kit, all the user has to do is prepare a solution of the materials in the first container means, form a dispersion of the cells he desires to encapsulate, add the solution to the processing medium, disperse the aqueous droplets to form a stable emulsion, add the crosslinking agent, and allow wall-forming to occur. The user may, of course, add any of the aforementioned optional steps.

The capsules of the invention are especially useful for the administration of cells to an animal, wherein the immune response of the animal towards the cell wishes to be minimized. Thus, hybridoma cells can be grown in an animal by injecting capsules comprising said cells into the animal. Drug delivery to an animal can be greatly facilitated by injecting the animal with capsules comprising cells which produce a pharmacologically active agent. Thus, recombinant bacteria which produce insulin, growth hormone or interferon could be injected into an animal and provide for a ready and continuous source of these active agents. Encapsulated pancreatic cells could be injected into a diabetic subject so as to provide a ready source of insulin. Cells which produce antibodies, enzymes and other biologically active materials can also be administered.

Of particular interest is the preparation of capsule or microcapsule walls from proteins originating in the animal to be used as host or subject of administration. This diminishes the possibility of immune response. For example, the use of BSA walls will facilitate the use of bovids as recipients, or the use of protein walls comprising human serum albumin facilitates administration of the capsules to humans.

The administration of the capsules can be by local administration, by intravenous, interperitoneal, or intramuscular injection, by infusion, perfusion, and the like.

Alternatively, the capsules used according to this invention have other uses. For example, they can serve as catalytic materials, in place of the heretofore used immobilized microbial cells or immobilized enzymes. They can be used for analytical purposes, by utilizing degradative encapsulated microorganisms to release a gas such as oxygen, which can then be monitored by means of an oxygen electrode, as is otherwise well-known in the art.

When the microcapsules are used therapeutically, the amount to be provided to the subject will depend on the age, sex, condition of the subject, other concurrent administrations, counter indications, and the like. For example, it is readily possible to calculate, for a given application, how much insulin or interferon should be released into the circulation over a given period of time, and accordingly inject the appropriate amount of microcapsules containing the desired cells.

A particularly useful capsule is one which is derived from immunoglobulins in part or as a whole as the protein wall-forming material. By choosing the specificity of the immunoglobulins, one can produce capsules which will be directed to antigenic sites complementary to the wall-containing antibodies, and transform the capsules into a directed carrier system for living cells.

Having now generally described this invention, the same will become better understood by reference to a specific example which is included herein for purposes of illustration only and is not intended to be limiting of the invention or of any embodiment thereof.

EXAMPLE

Preparation of Hybridoma Microcapsules

All of the microencapsulation equipment was first sterilized. Bovine serum albumin, BSA, (100 mg), was dissolved in 1 ml of RPMI 1640 culture media containing sodium bicarbonate, 2-mercaptoethanol, penicillin, streptomycin, fungizone, and 10% of heat inactivated fetal bovine serum. This solution was sterilized by passing it through a millipore filter (Type HA 0.45 $\mu$m, Millipore Corporation, Bedford, Mass.) into a sterile test tube. Next, 200 mg of polyethylene glycol, PEG, Carbowax 6,000, Fisher Scientific Company, Pittsburgh, Pa.) was dissolved in the BSA solution and a pellet containing about $10^6$ hybridoma cells was suspended in 0.5 ml of the BSA-PEG medium mixture.

This suspension was next added dropwise to 20 ml of sterile sesame oil contained in a 50 ml resin kettle, maintained at 37° C., and stirred at 1,200 rpm. A water-in-oil emulsion formed with aqueous microdroplets consisting of BSA, PEG, cells and culture media. One minute following the addition of the aqueous phase to the sesame oil, sebacoyl chloride (0.2 ml dissolved in 2 ml sesame oil) was added to the contents of the resin kettle. Two minutes after the sebacoyl chloride addition the stir rate was reduced from 1,200 rpm to 900 rpm. These conditions were maintained for 40 minutes to allow the sebacoyl chloride to crosslink the BSA to form the microcapsule walls. After 40 minutes the contents of the resin kettle were gently centrifuged to spin down the microcapsules. The supernatant was removed and the microcapsules were washed with fresh, sterile sesame oil to remove the residual sebacoyl chloride.

To transfer the microcapsules to culture media, the microcapsules were again centrifuged, the supernatant was removed, 2 ml of heptane was added to the microcapsule pellet, and this was quickly mixed with 5 ml of culture media. The mixture was then centrifuged; the supernatant was removed, and the microcapsule pellet was washed one more time with fresh culture medium, and the medium was adjusted to the proper pH.

Cell viability after the microencapsulation was demonstrated by incubating the microcapsules in neutral red. The microencapsulated cells stained red, indicating viability. In a second approach the microcapsules were broken open and the exposed cells were incubated with trypan blue. No staining of the cells indicated that they were viable. The cells are viable for at least 2 months.

Having now fully descibed this invention it will be understood that the same can be performed within a wide and equivalent range of parameters, conditions, materials and the like without affecting the spirit or scope of the invention or of any embodiment thereof.

What is claimed as new and intended to be covered by Letters Patent of the United States is:

1. A process for the encapsulation of living cells which comprises:
   (a) dispersing living cells in an aqueous solution of a capsule wall-forming protein;
   (b) forming aqueous droplets of said cell-containing dispersion in an aqueous-immiscible, cell compatible continuous processing medium;
   (c) crosslinking said protein with a crosslinking agent which is soluble in said continuous processing medium but substantially insoluble in said aqueous droplets thus forming crosslinked capsules, and adding to the formed crosslinked capsules a capsule wall degradation enzyme for a time sufficient to enlarge pore sizes in said walls to a predetermined average size.

2. The process of claim 1 wherein said aqueous solution also contains nutrients for said cells.

3. The process of claim 1 wherein said protein is selected from the group consisting of albumin, casein, collagen, gelatin, soy protein, gluten, and immunoglobulin.

4. The process of claim 1 wherein said solution also comprises an additional, enzyme-degradable material.

5. The process of claim 4 wherein said additional material is a polysaccharide, protein or nucleic acid.

6. The process of claim 1, wherein said cells are selected from the group consisting of animal, vegetable, microbiological, and artificially constructed cells.

7. The process of claim 4 wherein said cells are hybridoma cells.

8. The process of claim 4 wherein said cells are bacterial cells.

9. The process of claim 8 wherein said bacterial cells express a product coded by a non-bacterial gene which has been recombined into the DNA of said bacteria.

10. The process of claim 9 wherein said non-bacterial gene is a mammalian gene.

11. The process of claim 1 wherein said capsules have average diameters less than about 250 $\mu$m.

12. The process of claim 1 wherein said processing medium is vegetable or mineral oil.

13. The process of claim 1 wherein said processing medium is selected from the group consisting of peanut oil, sesame oil and cottonseed oil.

14. The process of claim 1 wherein said crosslinking agent is at least a bifunctional agent capable of reacting with amino, hydroxy, carboxy or thiol groups of proteins.

15. The process of claim 14 wherein said crosslinking agent is a diacid halide.

16. The process of claim 15 wherein said diacid halide has the formula:

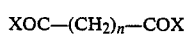

$$XOC-(CH_2)_n-COX$$

wherein X is a halide, and n is an integer from 4 to 12.

17. The process of claim 1 which also comprises the step of washing the crosslinked capsules with an aqueous insoluble solvent.

18. The process of claim 1 wherein said aqueous solution of capsule wall forming protein also comprises a water soluble poragenic compound.

19. The process of claim 18 wherein said poragenic compound is present in said solution at from 1 mg/ml to 1 g/ml.

20. The process of claim 18 wherein said compound is selected from the group consisting of poly(vinyl alcohol), carboxymethyl cellulose, poly(vinyl pyrrolidone), starch or glycol.

21. The process of claim 18 wherein said compound is a polyglycol having a molecular weight from 100 to 10,000.

22. The process of claim 1 wherein said enzyme is a proteolytic enzyme.

23. The process of claim 1 wherein said enzyme is a polysaccharide degrading enzyme, a DNase, an RNase, keratinase, cellulase, amylase or collagenase.

24. The method of claim 1 wherein said wall has sufficient porosity to allow the passage therethrough of molecules having molecular weights in the range up to 500,000, or particles with a diameter up to about 3,000 Å.

25. The method of claim 24 wherein said molecules are immunoglobulins.

26. The method of claim 25 wherein said immunoglobulins are monoclonal antibodies.

* * * * *